United States Patent [19]
Yamashita et al.

[11] Patent Number: 5,532,489
[45] Date of Patent: Jul. 2, 1996

[54] POSITRON IMAGING APPARATUS

[75] Inventors: Takaji Yamashita; Eiichi Tanaka, both of Hamamatsu, Japan

[73] Assignee: Hamamatsu Photonics K.K., Hamamatsu, Japan

[21] Appl. No.: 257,677

[22] Filed: Jun. 8, 1994

[30] Foreign Application Priority Data

Jun. 10, 1993 [JP] Japan .................................. 5-138740

[51] Int. Cl.$^6$ .................................................. G01T 1/17
[52] U.S. Cl. ........................................................ 250/363.03
[58] Field of Search ........................................ 250/363.03

[56] References Cited

U.S. PATENT DOCUMENTS

| | | | |
|---|---|---|---|
| 3,329,814 | 7/1967 | Anger | 250/363.03 |
| 3,502,873 | 3/1970 | Woronowicz | 250/366 |
| 4,743,764 | 5/1988 | Casey et al. | |
| 4,961,208 | 10/1990 | Okada | |
| 5,151,599 | 9/1992 | Monnet et al. | 250/363.03 |
| 5,285,073 | 2/1994 | Schelten et al. | 250/394 |

FOREIGN PATENT DOCUMENTS 60-188868  9/1985  Japan.

OTHER PUBLICATIONS

Yamamoto et al., Time–of–Flight Positron Imaging and the Resolution Improvement by an Interactive Method, IEEE Transactions of Nuclear Science, 1989, vol. 36, No. 1, pp. 998–1002.

*Primary Examiner*—Constantine Hannaher
*Attorney, Agent, or Firm*—Cushman Darby & Cushman

[57] ABSTRACT

Two γ-rays accompanying position annihilation are incident into γ-ray detectors in detector arrays set with a measured object inbetween. Electric pulse signals output from the γ-ray detectors are supplied to an annihilation presuming unit, which obtains a presumable event of positron annihilation by the coincidence counting conditions and which notifies an image reconstructing unit of annihilation occurrence notification and information of detectors. Electric pulse signals output from the γ-ray detectors are supplied to a time-of-flight difference measuring unit, which measures a difference of detection time between the detectors and notifies the image reconstructing unit of it. The image reconstructing unit obtains a presumable annihilation position based on the received information and stores it. A tomographic image of a specific portion is obtained by an algorithm for substantially compensating measurement errors, for example by the iterative process with the stored information.

18 Claims, 9 Drawing Sheets

POSITRON IMAGING APPARATUS

BACKGROUND OF THE INVENTION

1. Field of the Invention

The present invention relates to a positron imaging apparatus for determining an internal substance distribution in a body to be measured.

2. Related Background Art

Attention is being drawn to positron imaging apparatus for determining the internal substance distribution in a body to be measured. With the positron imaging apparatus, chemical compounds labeled with radioisotopes to emit positrons are put into the body to be measured such as a human body or an animal body, and measurement is made for a pair of γ-rays which are produced when (pair) annihilation between a positron emitted from the radioisotope annihilates combining with an electron in an ordinary substance, whereby the internal substance distribution is determined in the measured body. Energy of each γ-ray in the annihilation is approximately the same as the mass energy (0.511 MeV) of a positron or an electron. The two γ-rays are emitted in opposite directions to each other. A distribution of the labeled substances inside the measured body is determined by measuring such the annihilation γ-ray pairs within the measured body. In view of the energy of each γ-ray and the present status of measuring means, a general measuring system is one for letting the photon emit scintillation in a γ-ray detecting element (so called scintillator) and thereafter detecting the scintillation with a photodetector.

Among apparatus employing the above method is a positron CT apparatus (or PET (Positron Emission Tomography) apparatus). Such a PET apparatus is so constructed that a number of γ-ray detectors each composed of a γ-ray detecting element (for example, a BGO scintillator) and a photodetector are arranged in multi-layer ring structure around a certain axis. When two γ-ray detectors detect γ-rays at the above specific energy (0.511 MeV) in coincidence, an event of positron annihilation is recognized. Spatially connecting between the coincidence detectors can give a presumable line on which the position of annihilation is located. The substance distribution in the measured body is determined by obtaining a number of presumable lines for annihilation and performing arithmetic processing.

There are also reports on positron probe apparatus (hereinafter referred to as TOF positron probe) utilizing a time of flight of γ-ray as an apparatus employing the method for detecting two γ-rays accompanying an event of positron-electron annihilation, which measures a difference between γ-ray arrival times at two detectors for detecting two annihilation γ-rays (M. Yamamoto et al.: IEEE TRANSACTION ON NUCLEAR SCIENCE, Vol. 36, No. 1, 1989, pp 998–1002, for example). The TOF positron probe determines the substance distribution in a measured body by obtaining a lot of presumable annihilation events and performing arithmetic processing.

SUMMARY OF THE INVENTION

The present invention has been accomplished to solve the above problems and an object of the present invention is to provide a positron imaging apparatus which can effectively measure information about an interest portion, matching with the position and the size of the specific interest portion in a measured body.

A positron imaging apparatus of the present invention is so arranged that two detector arrays each composed of γ-ray detectors are set in an opposed relation with a measured body inbetween, matching with the position and the size of a specific interest portion in the measured body. In measurement of the specific portion, the arrangement and the setting position are determined to be optimized with necessity, depending upon the distance between the measured body and the detector arrays. The first positron imaging apparatus of the present invention reconstructs an image by the so-called focal plane method, based on information from detectors which have detected two γ-rays emitted with positron annihilation. The second positron imaging apparatus of the present invention reconstructs an image by the so-called TOF method or a modified TOF method by iterative reconstruction algorithm, based on information from detectors which have detected two γ-rays emitted with positron annihilation and information of a difference between γ-ray arrival times at each detector.

In more detail, the first positron imaging apparatus of the present invention comprises (a) a first detector array comprising a first number of γ-ray detectors set therein with a first detector size, (b) a second detector array arranged in an opposed relation to the first detector array with a measured body inbetween, and comprising a second number of γ-ray detectors set therein with a second detector size, (c) annihilation presuming means for receiving signals reflecting energy of incident γ-rays, output from the first detector array and the second detector array to determine a presumable γ-ray pair emitted with positron annihilation, and (d) image reconstructing means for, in synchronization with annihilation occurrence notification output from the annihilation presuming means, collecting and storing receiving detector information on the first detector array and receiving detector information on the second detector array for the presumed γ-ray pair emitted with positron annihilation and performing an arithmetic operation according to an image reconstruction algorithm based on information about a line passing through a position of annihilation occurrence calculated from the stored detector information; in which in operation, there is at least one difference between the first number and the second number, between the first detector size and the second detector size, or between a detector pitch in the first detector array and a detector pitch in the second detector array and coincidence counting is carried out for every opposing γ-ray detector pair.

The apparatus may be arranged with such a feature that the image reconstruction algorithm is the focal plane method, in which a virtual focal plane is first set, an intersection is obtained between the virtual focal plane and the position of each annihilation occurrence, and an image is reconstructed taking the degree of concentration in a distribution of the intersections into consideration.

The second positron imaging apparatus of the present invention comprises (a) a first detector array comprising a first number of γ-ray detectors set therein with a first detector size, (b) a second detector array arranged in an opposed relation to the first detector array with a measured body inbetween, and comprising a second number of γ-ray detectors set therein with a second detector size, (c) annihilation presuming means for receiving signals reflecting energy of incident γ-rays, output from the first detector array and the second detector array to determine a presumable γ-ray pair emitted with positron annihilation, (d) time-of-flight difference measuring means for measuring a time between a γ-ray arrival time at the first detector array and a γ-ray arrival time at the second detector array with regard to detection signals of two γ-rays with annihilation, output from the first detector array and the second detector array, and (e) image reconstructing means for, in synchronization with annihilation occurrence notification output from the annihilation presuming means, collecting receiving detector information on the first detector array and receiving detector information on the second detector array for the presumable γ-ray pair emitted with electron-positron annihilation and time-of-flight difference information output from the time-of-flight difference measuring means, calculating a position of annihilation occurrence using the receiving detector information and the time-of-flight difference information, storing the position of annihilation occurrence, and performing an arithmetic operation according to an image reconstruction algorithm based on the stored annihilation position; in which in operation, there is at least one difference between the first number and the second number, between the first detector size and the second detector size, or between a detector pitch in the first detector array and a detector pitch in the second detector array, and coincidence counting is carried out for every opposing γ-ray detector pair.

Here, the apparatus may be arranged with such a feature that the predetermined image reconstruction algorithm is the iterative method, in which a selected image is employed as an initial image and correction of image is iteratively conducted taking into consideration the spatial resolution.

Also, the first and second positron imaging apparatus of the present invention may be arranged with such a feature that if a distance between the first detector array and the measured body is longer than that between the second detector array and the measured body the first number is greater than the second number while if the distance between the first detector array and the measured body is shorter than that between the second detector array and the measured body the first number is smaller than the second number. Here, the apparatus may have such a feature that the first detector size and the second detector size are almost equal to each other and a ratio of the distance between the first detector array and the measured body to the first number is almost equal to a ratio of the distance between the second detector array and the measured body to the second number.

Further, the first and second positron imaging apparatus of the present invention may be arranged with such a feature that if the distance between the first detector array and the measured body is longer than the distance between the second detector array and the measured body the detector pitch of γ-ray detectors in the first detector array is greater than the detector pitch of γ-ray detectors in the second detector array while if the distance between the first detector array and the measured body is shorter than the distance between the second detector array and the measured body the detector pitch of γ-ray detectors in the first detector array is smaller than the detector pitch of γ-ray detectors in the second detector array. Here, the apparatus may have such a feature that if the distance between the first detector array and the measured body is longer than the distance between the second detector array and the measured body the first detector size is greater than the second detector size while if the distance between the first detector array and the measured body is shorter than the distance between the second detector array and the measured body the first detector size is smaller than the second detector size.

When a positron-labeled compound is put into a body to be measured (for example a human body), the dosage of the compound gathers in a specific portion, reflecting the property of the compound and the physiological condition of the body. A positron emitted from the compound effects annihilation with an electron in a surrounding substance to produce two γ-rays each at the energy of 0.511 MeV.

In the first positron imaging apparatus of the present invention, the two detector arrays with a plurality of γ-ray detectors arranged therein are set as opposed to each other, considering the size of the specific portion, the position of the specific portion inside the measured body, the size of a receiving surface of γ-ray detectors, the required measurement accuracy (spatial resolution) and the detection efficiency (measurement field). When with positron annihilation two γ-rays are incident into γ-ray detectors in the respective detector arrays, they are converted therein into electric pulse signals according to the energy of incident γ-rays.

The electric pulse signals output from the γ-ray detectors are input into the annihilation presuming means and it is first checked whether the energy of incident γ-ray is about 0.511 MeV. It is then checked one by one for γ-rays at the energy of about 0.511 MeV whether there is a pair which were incident into the detector arrays within an predetermined time difference (a few–20 ns) which could permit the two γ-rays to come from the same annihilation event (which is so called as coincidence counting), considering the size of the specific portion, the distances between the detectors and the specific portion, and the speed of light. When the above two conditions are satisfied, the annihilation presuming means presumes that an event of positron annihilation occurred and notifies the image reconstruction means of information on the γ-ray incident detectors together with the annihilation occurrence notification.

The image reconstructing means obtains a presumable line on which the position of annihilation could be present, by connecting center points of the two detectors in coincidence, based on the input detector information and stores the line information as one event. During or after measurement of annihilation, the algorithm as called as the focal plane method is carried out with the stored information about event such that a virtual focal plane is hypothetically determined, images are reconstructed on the virtual focal plane under the preposition that all annihilation events occurred on the virtual focal plane, and only images which could be deemed as focused are selected, whereby a tomographic image of the specific portion can be obtained.

In the second positron imaging apparatus of the present invention, similarly as the above first positron imaging apparatus, the two detector arrays with a plurality of γ-ray detectors arranged therein are set as opposed to each other, considering the size of the specific portion, the position of the specific portion inside the measured body, the size of a receiving surface of γ-ray detectors, the required measurement accuracy (spatial resolution) and the detection efficiency (measurement field). When with positron annihilation two γ-rays are incident into γ-ray detectors in the respective detector arrays, they are converted therein into electric pulse signals according to the energy of incident γ-rays.

The electric pulse signals output from the γ-ray detectors are input into the annihilation presuming means and it is first checked whether the energy of incident γ-ray is about 0.511 MeV. It is then checked one by one for γ-rays at the energy of about 0.511 MeV whether there is a pair which were incident into the detector arrays within an incident time difference which could permit the two γ-rays to come from the same annihilation, considering the size of the specific portion, the distances between the detectors and the specific portion, and the speed of light. When the above two points are satisfied, the annihilation presuming means presumes that an event of positron annihilation occurred and notifies the image reconstruction means of information on the γ-ray incident detectors together with the annihilation occurrence notification.

Also, the electric pulse signals output from the γ-ray detectors are supplied to the time-of-flight difference measuring means, which, with regard to the detection signals of two γ-rays with annihilation, output from the first detector array and second detector array, measures a time between the γ-ray arrival time in the first detector array and the γ-ray arrival time in the second detector array and notifies the image reconstructing means of it.

The image reconstructing means obtains a presumable line on which the position of annihilation could be present, by connecting the center points of γ-ray incident surfaces of the two detectors, based on the information on the two detectors supplied from the annihilation presuming means, and a presumable annihilation position on the presumable line, and stores the annihilation position information as one event. During or after measurement of annihilation a tomographic image of the specific portion is obtained by the algorithm for substantially compensating measurement errors by the iterative method with the stored position information about event.

The first and second positron imaging apparatus of this invention may have a driving means. The driving means moves the first detector array and the second detector array of the positron imaging apparatus to scan the measured object. The driving means to the positron imaging apparatus, for example, is implemented as shown in U.S. Pat. No. 4,961,208 or U.S. Pat. No. 4,743,764.

As detailed above, the first positron imaging apparatus of the present invention is so arranged that the two detector arrays with a plurality of γ-ray detectors arranged therein are opposed to each other, taking into consideration the size of the specific interest portion in the measured body, the position of the specific portion in the measured body, the size of the receiving surface of γ-ray detectors, the required measurement accuracy (spatial resolution) and the detection efficiency (measurement field). Using the thus constructed detecting unit, a line passing through the annihilation position between electron and positron is presumed by the coincidence counting and an image is reconstructed by the focal plane method. Therefore, a tomographic image can be obtained with excellent resolution and image quality by such a low-cost and compact apparatus as compared with the conventional PET apparatus.

Also, the second positron imaging apparatus of the present invention is so arranged that the two detector arrays with a plurality of γ-ray detectors arranged therein are opposed to each other, taking into consideration the size of the specific interest portion in the measured body, the position of the specific portion in the measured body, the size of the receiving surface of γ-ray detectors, the required measurement accuracy (spatial resolution) and the detection efficiency (measurement field). Using the thus constructed detecting unit, the annihilation position between electron and positron is presumed by the coincidence counting method and the TOF method and an image is reconstructed by the iterative reconstructure algorithm. Therefore, a tomographic image with excellent resolution and image quality can be obtained by such a compact apparatus as compared with the conventional PET apparatus.

In the case that the measurement is conducted when a body to be measured lies down on the bed, the lower detector (under the bed) under the body to be measured can be set near the body to be measured; however, the upper detector is needed to be separated by some length because of the unevenness of the body to be measured. (This is required especially in the case of scanning the whole body.)

Further, in the case that the blood pressure or the electrocardiogram of the body to be measured is taken, the upper detector is needed to be separated from the body to be measured in order to set the probes to the body to be measured. In such a case, in the same way as the present invention, a space between the upper detector arrays is set wide and a space between the lower detector arrays is set narrow, so that sampling at a position of the body to be measured is optimum and the image is improved.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

DESCRIPTION OF THE PREFERRED EMBODIMENTS

Figure 1:
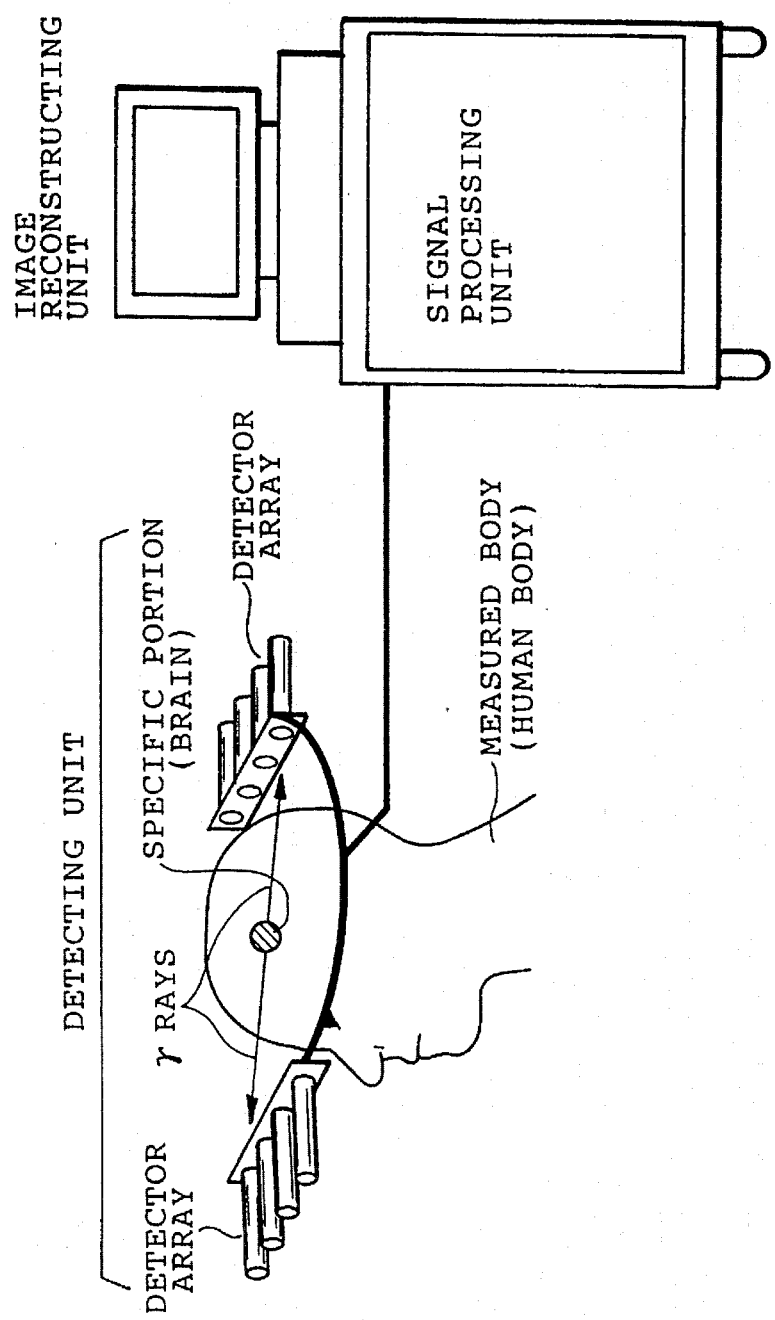
FIGS. 1 and 2 are schematic structural diagrams to show a positron imaging apparatus of the present invention.
Figure 2:
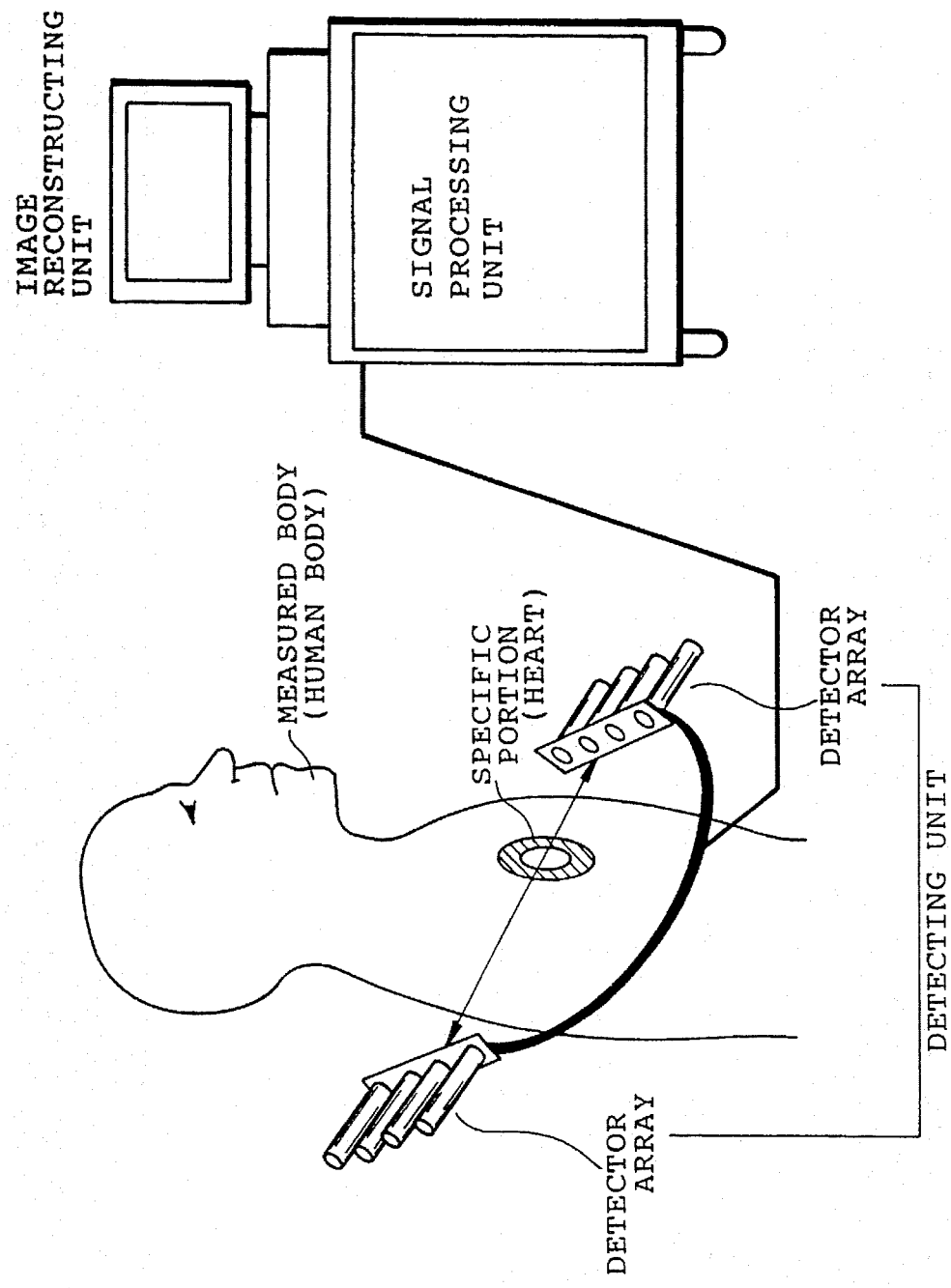

Before individually describing the embodiments according to the present invention, brief description is presented of positron imaging apparatus of the present invention. FIGS. 1 and 2 are schematic structural diagrams to show a positron imaging apparatus according to the present invention. FIG. 1 shows the structure of the apparatus where a body to be measured is a human body and a specific portion as an object to be measured is a part of brain and FIG. 2 shows the scheme of the apparatus where a body to be measured is a human body and a specific portion as an object to be measured is the heart.

As shown in FIGS. 1 and 2, the positron imaging apparatus of the present invention is composed of a detecting unit composed of two detector arrays, a signal processing unit for receiving and processing signals output from the detecting unit, and an image reconstructing unit for storing information output from the signal processing unit and processing the stored information data to reconstruct an image. In the first positron imaging apparatus of the present invention the signal processing unit is constructed of an annihilation presuming unit for obtaining a presumable event of annihilation occurrence by the coincidence counting method. In the second positron imaging apparatus of the present invention the signal processing unit is constructed of an annihilation presuming unit for obtaining a presumable event of annihilation occurrence by the coincidence counting method and a time-of-flight difference measuring unit for measuring a difference in time of flight of from occurrence to detection of two γ-rays.

Now, the embodiments of the present invention will be described with reference to the accompanying drawings. In the description of the drawings same elements will be denoted by same reference numerals and redundant description will be omitted.

First Embodiment

This apparatus belongs to the first positron imaging apparatus of the present invention, in which the coincidence counting method is used for identification of annihilation between electron and positron to determine a line passing through a position of annihilation.

Figure 3:
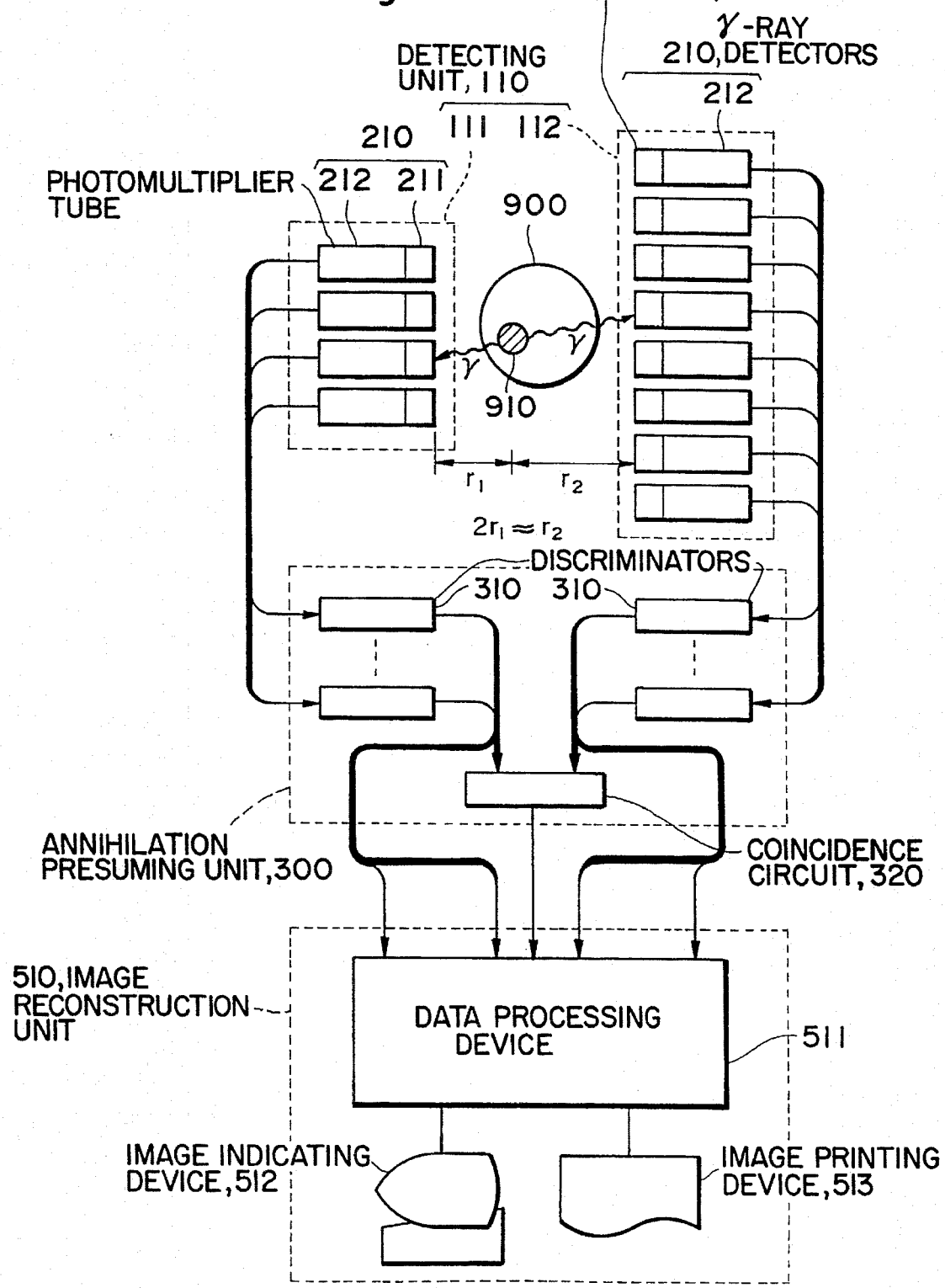
FIG. 3 is a structural drawing to show a positron imaging apparatus in a first embodiment of the present invention.

FIG. 3 is a structural drawing to show a positron imaging apparatus of the present embodiment. As shown, the positron imaging apparatus of the present invention is composed of a detecting unit 110 for detecting incident γ-ray, an annihilation presuming unit 300 for receiving signals output from the detecting unit 110 and obtaining presumable events of annihilation occurrence by the coincidence counting method, and an image reconstructing unit 510 for receiving and storing detector information signals and annihilation detection signals output from the annihilation presuming unit 300 and processing the stored line information data by the focal plane method to reconstruct an image.

Here, the detecting unit 110 is constructed such that a detector array 111 and a detector array 112 are opposed to each other. Each detector array is composed of a plurality of γ-ray detectors 210 (four detectors and eight detectors in the shown apparatus) one-dimensionally aligned. Each γ-ray detector 210 is composed of $BaF_2$ scintillator 211 and a photomultiplier tube 212. The γ-ray detectors used in this apparatus have same specifications. The number of γ-ray detectors in each detector array is determined in proportion to a distance between a specific portion as a measured object and each detector array, considering the size of the specific portion, the position of the specific portion in a measured body, the size of receiving surface of γ-ray detectors 210, the required measurement accuracy (spatial resolution) and the detection efficiency (measurement field).

The annihilation presuming unit 300 is composed of discriminators 310 set for associated γ-ray detectors 210 to check if energy of incident γ-ray is about 0.511 MeV, and a coincidence circuit 320 for receiving signals output from the all discriminators 310. The coincidence circuit 320 makes a decision as to if each detector array detects a γ-ray with energy of about 0.511 MeV within a difference of time of incidence between two γ-rays accompanying a same event of annihilation.

The image reconstructing unit 510 is composed of a data processing device 511 for receiving and storing signals output from the annihilation presuming unit 300 and performing arithmetic processing, an image indicating device 512 for indicating a tomographic image as an operation result of the data processing device 511, and an image printing device 513 for printing the tomographic image.

Two γ-rays appearing upon positron annihilation in a specific portion 910 in a measured body 900 are incident into a γ-ray detector 210 in the detector array 111 and a γ-ray detector 210 in the detector array 112. An incident γ-ray causes a scintillator 211 to emit scintillation photons, and the scintillation photons enter a photomultiplier tube 212 to be converted into an electric pulse signals with a crest value (amplitude) according to the energy of incident γ-ray.

Electric pulse signals output from the respective γ-ray detectors 210 are supplied to the annihilation presuming unit 300. The annihilation presuming unit 300 first checks if the energy of each incident γ-ray is about 0.511 MeV through the discriminators 310 a threshold range of which is set near the electric signal pulse height according to the incident γ-ray energy of about 0.511 MeV. Then the coincidence circuit 320 checks if a γ-ray with energy of about 0.511 MeV was incident into each detector array within a difference of time of incidence which two γ-rays from same annihilation could have, considering the size of the specific portion, the distance between each detector and the specific portion and the speed of light. If the above two points are satisfied, the annihilation presuming unit 300 presumes that an event of positron annihilation has occurred and notifies the image reconstructing unit 510 of the fact and output signals from the discriminators 310.

When the image reconstructing unit 510 receives the annihilation occurrence notification (i.e., event occurrence notification) output from the annihilation presuming unit 300, the data processing device 511 receives the outputs from the discriminators 310 as parallel digital signals. In this case, the digital signals each include two significant bits and other insignificant bits. Among the occurring events as measured by the detecting unit 110 and the annihilation presuming unit 300, the data processing device 511 stores events reported from the annihilation presuming unit 300.

During or after measurement of annihilation the data processing device 511 processes the stored information concerning the events by the following procedure to reconstruct an image. First, the data processing device 511 reads out the stored information of an event (which is data with significant bit corresponding to a γ-ray detector in each detector array) and connects the centers of incident surfaces of γ-ray detectors corresponding to the significant bits to calculate a line passing through a position of annihilation occurrence. Then the device hypothetically determines a virtual focal plane. Assuming that annihilation has occurred on the virtual focal plane, it makes a plot thereon under a preposition that the annihilation occurrence position is at an intersection between the virtual focal plane and the calculated line. The above processes of from the reading-out of event information to the preposition plot are repeated for all stored events.

Figure 4:
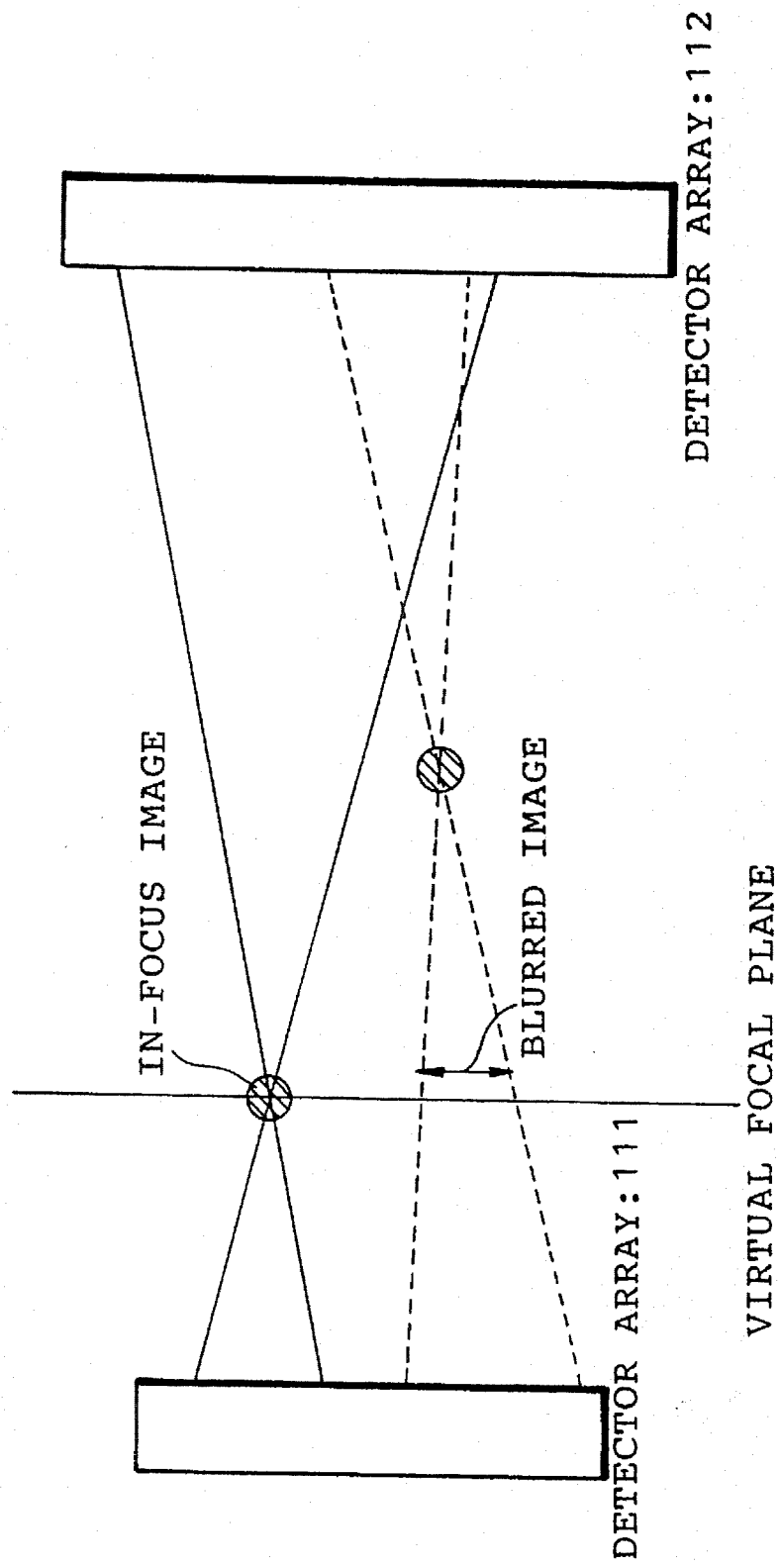
FIG. 4 is an explanatory drawing to illustrate the focal plane method.

As shown in FIG. 4, if a point of annihilation is actually present on or near the virtual focal plane, a plurality of plots for annihilation events at the annihilation point are concentrated there as if to be focused. On the other hand, if the annihilation point is present actually at a point apart from the virtual focal plane, the plots are not concentrated there as if to be unfocused, providing a blurred image. Subsequently, the device selects only images which can be judged as in focus, obtaining a tomographic image on the virtual focal plane for the specific portion. The tomographic image is provided to a user by indicating it on the image indicating device 512 or by printing it by the image printing device 513.

Subsequently, another virtual focal plane is set to obtain a tomographic image thereon, obtaining a tomographic image on another virtual focal plane.

Further, moving the detecting unit to scan, the three-dimensional structure of the specific portion can be known. If the detector arrays are arranged in two dimensions, the three-dimensional structure of the specific portion can be observed without scan.

Second Embodiment

The positron imaging apparatus of the present embodiment belongs to the first positron imaging apparatus of the present invention, similarly as the first embodiment, in which the coincidence counting method is used for identification of annihilation between electron and positron to determine a line passing through the annihilation position.

Figure 5:
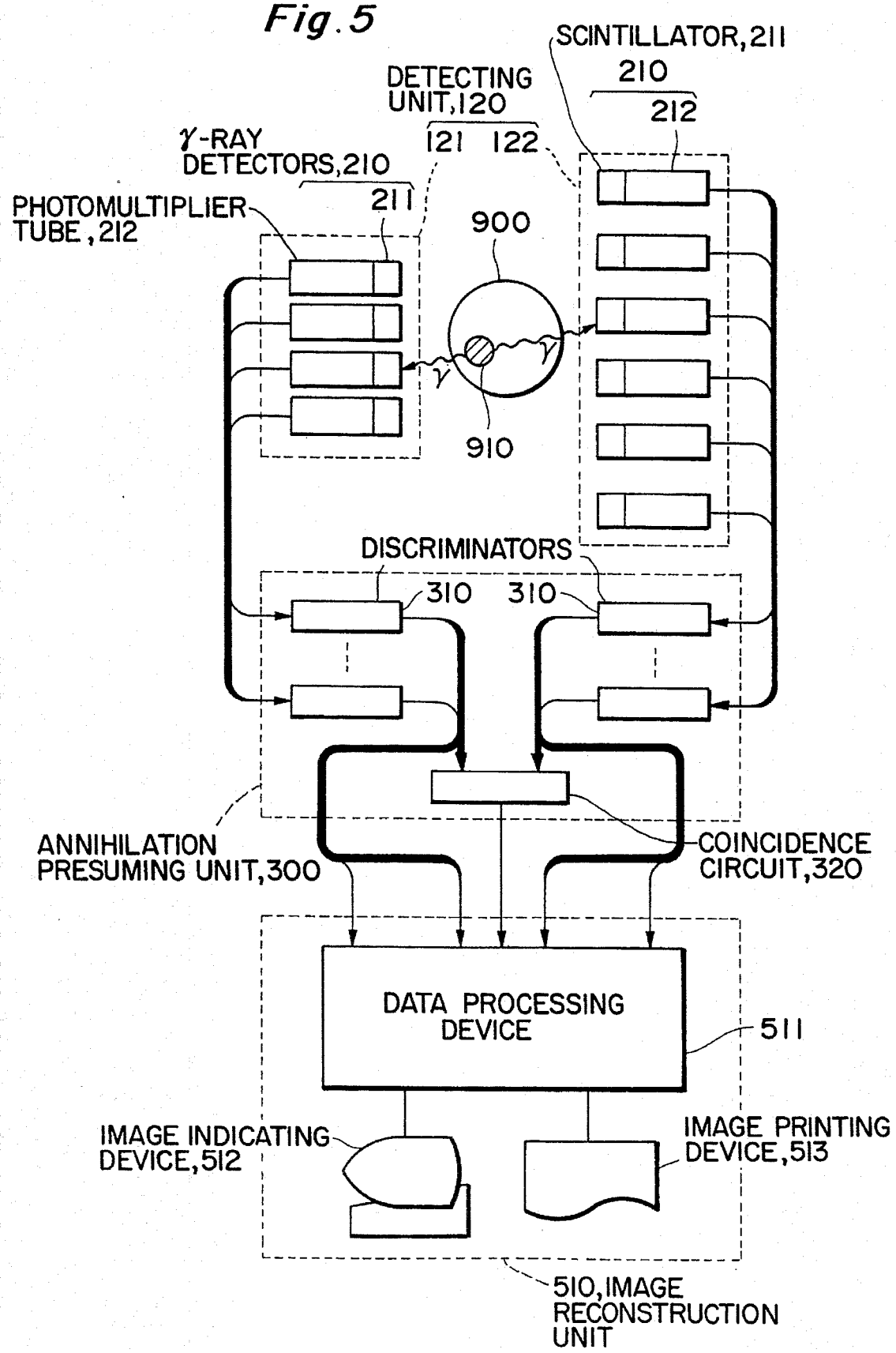
FIG. 5 is a structural drawing to show a positron imaging apparatus in a second embodiment of the present invention.

FIG. 5 is a structural drawing to show a positron imaging apparatus of the present embodiment. The structure of this apparatus is the same as the apparatus of the first embodiment except for the structure of the detecting unit. In the detecting unit 110 of the apparatus of the first embodiment the two detector arrays each are composed of γ-ray detectors of same specifications in a number proportional to the distance between the specific portion as a measured object and each detector array. On the other hand, the positron imaging apparatus of the present embodiment has such a detecting unit 120 that a solid angle of outer edge of detector array 121 as viewed from the specific portion is approximately equal to a solid angle of outer edge of detector array 122 as viewed from the specific portion and that a setting density of γ-ray detectors 210 in the detector array 121 closer to the specific portion as a measured object is set greater than a setting density of γ-ray detectors 210 in the detector array 122 farther to the specific portion.

The focal plane method as the image reconstruction method was described in the first embodiment and is also used in the apparatus of the present embodiment, which is more effective to judgement of in-focus state as the solid angle of outer edge of each detector array as viewed from the specific portion as a measured object increases. The apparatus of the present embodiment realizes an apparatus which is also effective to employ the focal plane method with a decreased number of γ-ray detectors 210 in the detector array 122 disposed more distant from the specific portion. Although the apparatus of the present embodiment has such a disadvantage that the γ-ray detection efficiency is lower than that in the apparatus of the first embodiment, it has an advantage of decreasing the total number of γ-ray detectors 210.

Two γ-rays appearing upon positron annihilation occurred in the specific portion in the measured body enter a γ-ray detector 210 in the detector array 121 and a γ-ray detector 210 in the detector array 122, respectively. After that, similarly as in the first embodiment, annihilation events are subjected to selection in the annihilation presuming unit 300 and data processing is carried out in the image reconstructing unit 510 to obtain a tomographic image.

If the detector arrays are arranged in two dimensions, the three-dimensional structure of the specific portion can be observed without scan, similarly as in the first embodiment.

Third Embodiment

This apparatus belongs to the first positron imaging apparatus of the present invention, similarly as the first embodiment, in which the coincidence counting method is used for identification of annihilation to determine a line passing through an annihilation position.

Figure 6:
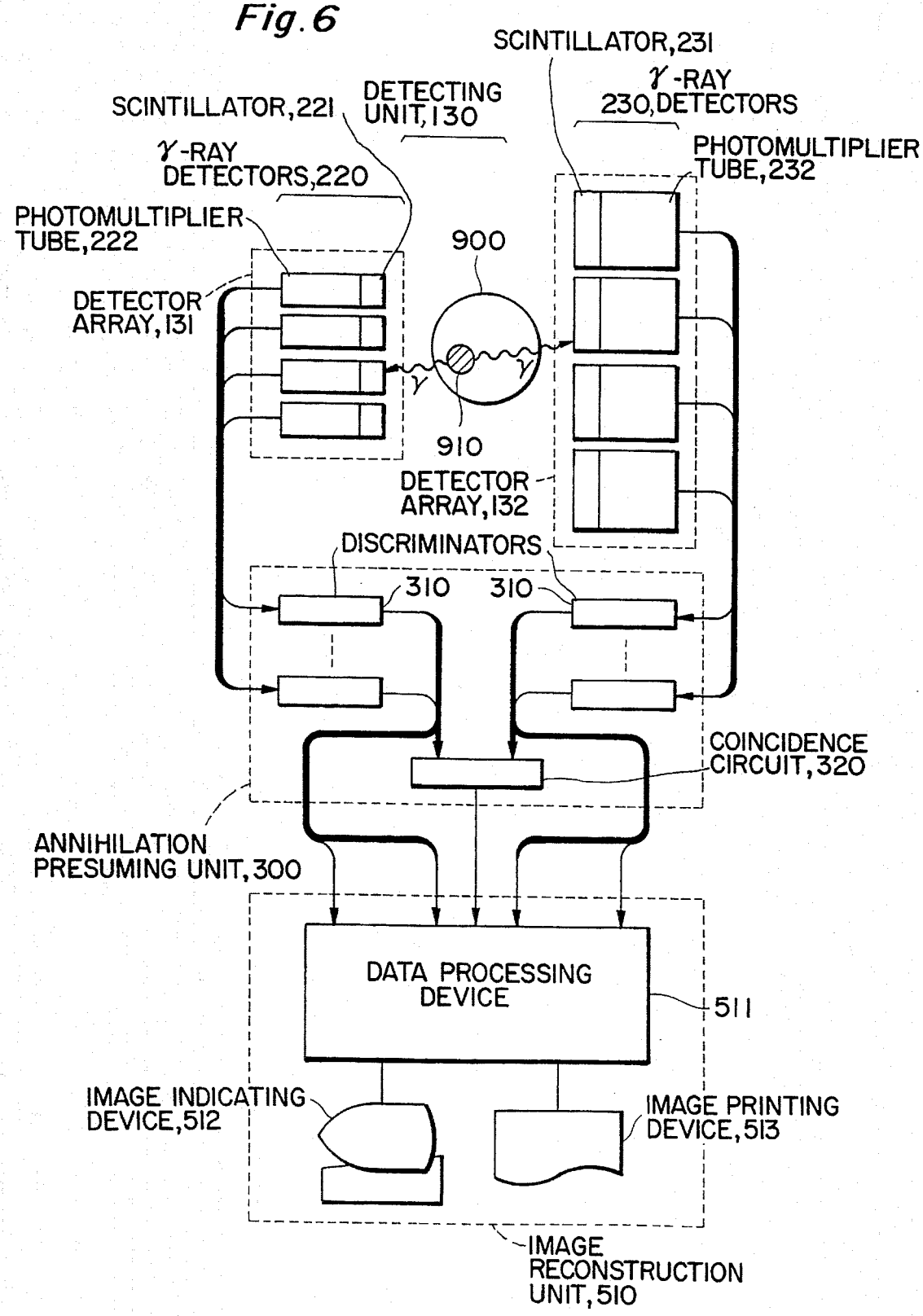
FIG. 6 is a structural drawing to show a positron imaging apparatus in a third embodiment of the present invention.

FIG. 6 is a structural drawing to show a positron imaging apparatus of the present embodiment. The structure of the apparatus is the same as the apparatus of the first embodiment except for the structure of the detecting unit. In the detecting unit 110 in the apparatus of the first embodiment, the two detector arrays each are composed of γ-ray detectors of same specifications, whereas a detecting unit 130 in the positron imaging apparatus of the present embodiment is so arranged that γ-ray detectors 220 constituting a detector array 131 and γ-ray detectors 230 constituting a detector array 132 have different detector sizes, i.e., that a detector size of γ-ray detectors 220 in the detector array 131 closer to the specific portion as a measured object is set smaller than a detector size of γ-ray detectors 230 in the detector array 132 farther to the specific portion. Here, the γ-ray detectors 220 each are composed of a $BaF_2$ scintillator 221 and a photomultiplier tube 222 and the γ-ray detectors 230 each are composed of a $BaF_2$ scintillator 231 and a photomultiplier tube 232.

Considering a coincidence counting detector pair of an arbitrary γ-ray detector 220 in the detector array 131 and an arbitrary γ-ray detector 230 in the detector array 132, the spatial resolution near the specific portion substantially depends upon a solid angle to view each γ-ray detector from the specific portion. The detection efficiency of two γ-rays appearing upon annihilation in the specific portion also depends upon the solid angle to view each γ-ray detector from the specific portion. Meanwhile, the solid angle to view each γ-ray detector from the specific portion is proportional to a distance from the specific portion to each γ-ray detector. Accordingly, setting the detector size in proportion with the distance from the specific portion, measurement is possible without lowering the detection efficiency of γ-rays and without lowering the spatial resolution near the specific portion as a measured object. Even if the detector size is not proportional to the distance from the specific portion but if the detector size is increased at a ratio smaller than the proportion with an increase in distance, the detection efficiency can be secured without lowering the spatial resolution.

Two γ-rays appearing upon positron annihilation occurred in the specific portion in the measured object enter a γ-ray detector 220 in the detector array 131 and a γ-ray detector 230 in the detector array 132, respectively. After that, similarly as in the first embodiment, annihilation events are subjected to selection in the annihilation presuming unit 300 and data processing is carried out in the image reconstructing unit 510 to obtain a tomographic image.

If the detector arrays are arranged in two dimensions, the three-dimensional structure of the specific portion can be observed without scan, similarly as in the first embodiment.

Fourth Embodiment

This apparatus belongs to the second positron imaging apparatus of the present invention, in which the coincidence counting method is used for identification of annihilation to determine an annihilation position in combination with the TOF method.

Figure 7:
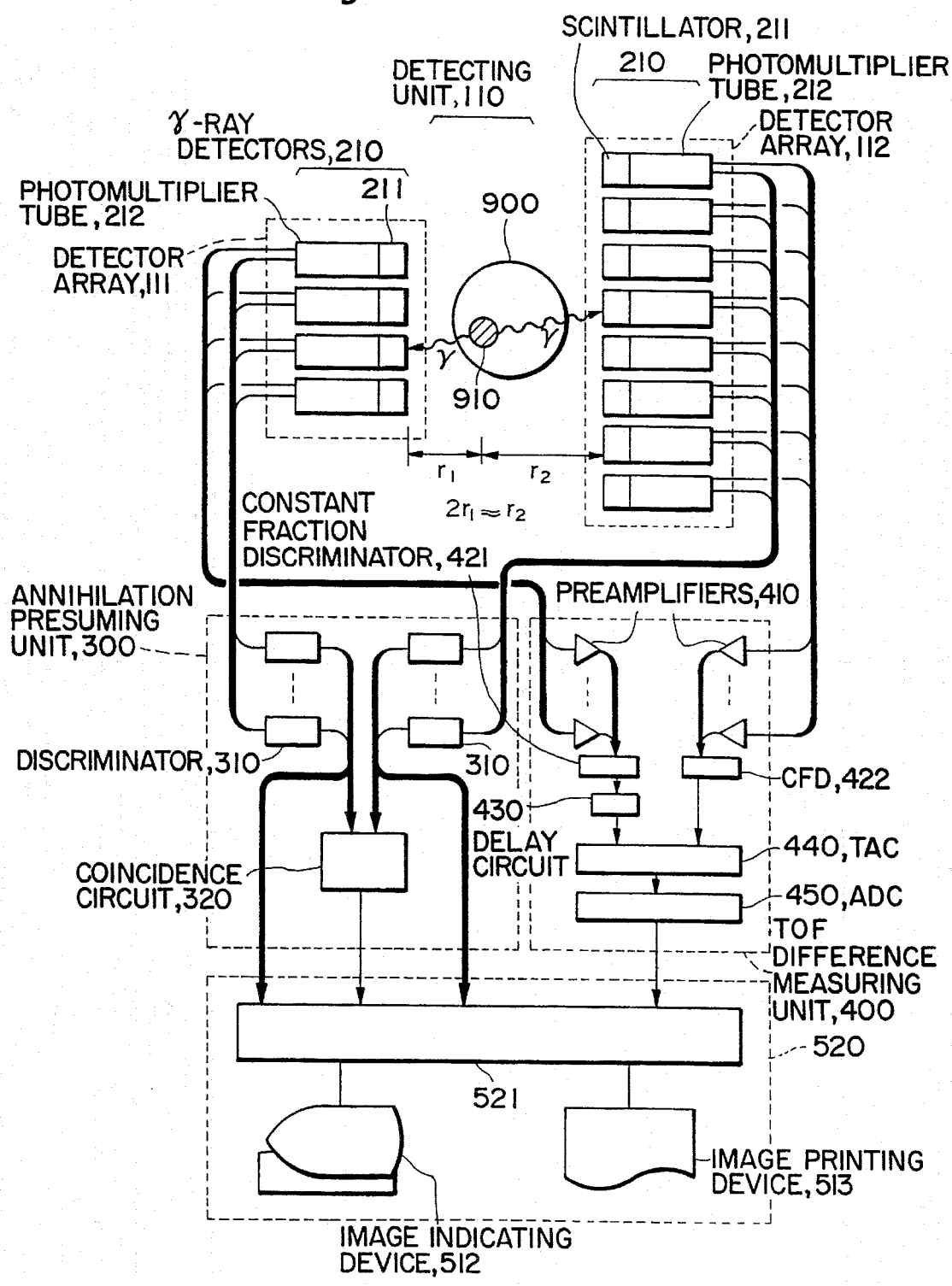
FIG. 7 is a structural drawing to show a positron imaging apparatus in a fourth embodiment of the present invention.

FIG. 7 is a structural drawing to show a positron imaging apparatus of the present embodiment. As shown, the positron imaging apparatus of the present invention is composed of a detecting unit 110 for detecting incident γ-ray, an annihilation presuming unit 300 for receiving signals output from the detecting unit 110 and obtaining presumable events of annihilation occurrence by the coincidence counting method, a time-of-flight difference measuring unit 400 for receiving signals output from the detecting unit 110 and obtaining a time difference between signal bundles of output signals from the γ-ray detectors in the respective detector arrays, and an image reconstructing unit 520 for receiving annihilation occurrence signals and detector information signals output from the annihilation presuming unit 300, and time difference information output from the time-of-flight difference measuring unit 400, storing the received data as annihilation position information, and processing the stored position information data by the iterative method to reconstruct an image.

Here, the detecting unit 110 and the annihilation presuming unit 300 are constructed in the same manner as in the first embodiment.

The time-of-flight difference measuring unit 400 is composed of preamplifiers 410 each provided for a corresponding γ-ray detector 210 to receive an output signal from each γ-ray detector 210, constant fraction discriminators (hereinafter referred to as CFD) 421 and 422 for receiving the output signals from the preamplifiers 410 in bundle for each detector array, a time to amplitude converter (hereinafter referred to as TAC) 440 for receiving an output signal from the CFD 422 and an output signal from a delay circuit 430 and converting a time difference between the two output signals into a crest value (amplitude), and an analog-to-digital converter (hereinafter referred to as ADC) 450 for digitalizing the amplitude of signal output from the TAC 440.

The image reconstructing unit 520 is constructed substantially in the same manner as the image reconstructing unit 510 in the apparatus of the first embodiment, but is different in a method for reconstructing an image therefrom and therefore different in the data processing device as an operational resource.

Two γ-rays appearing upon positron annihilation in a specific portion 910 in a measured body 900 are incident into a γ-ray detector 210 in the detector array 111 and a γ-ray detector 210 in the detector array 112. An incident γ-ray causes a scintillator 211 to emit scintillation photons, and the scintillation photons enter a photomultiplier tube 212 to be converted into an electric pulse signal with a crest value (amplitude) according to the energy of incident γ-ray.

Electric pulse signals output from the respective γ-ray detectors 210 are supplied to the annihilation presuming unit 300. The annihilation presuming unit 300 first checks if the energy of each incident γ-ray is about 0.511 MeV through the discriminators 310 a threshold range of which is set near the electric signal pulse height according to the incident γ-ray energy of about 0.511 MeV. Then the coincidence circuit 320 checks if a γ-ray with energy of about 0.511 MeV was incident into each detector array within a difference of time of incidence which two γ-rays from the same annihilation could have, considering the size of the specific portion, the distance between each detector and the specific portion and the speed of light. If the above two points are satisfied, the annihilation presuming unit 300 presumes that an event of positron annihilation has occurred and notifies the image reconstructing unit 520 of the fact and output signals from the discriminators 310.

Also, the electric pulse signals output from the respective γ-ray detectors 210 are supplied to the time-of-flight difference measuring unit 400. Each input signal is let to pass through a preamplifier 410 and thereafter the signals are bundled for each detector array. A bundled signal group on the detector array 111 side is supplied to the CFD 421 and a bundled signal group on the detector array 112 side to the CFD 422. The CFD 421 converts the input signal group into a fast timing signal and outputs it. The fast timing signal output from the CFD 421 is let to pass through the delay circuit 430 to be given a delay of constant time and then to be supplied to the TAC 440. The CFD 422 converts the input signal group into a fast timing signal and outputs it to the TAC 440. The TAC 440 converts the two input timing signals into a pulse signal having an amplitude proportional to an input time difference between them. The pulse signal is supplied to the ADC 450 to be digitalized and the digital data is supplied to the image reconstructing unit 520.

When the image reconstructing unit 520 receives the annihilation occurrence notification (i.e., event occurrence notification) output from the annihilation presuming unit 300, the data processing device 521 receives the output signal from ADC 450 representing a time-of-flight difference and the output signals from the discriminators 310 representing two γ-ray detectors which have detected the annihilation events, as parallel digital signals. In this case, the output signals from the discriminators 310 each are a digital signal with two significant bits and other insignificant bits. For the annihilation events judged as possibly occurred from the measurement results by the detecting unit 110 and annihilation presuming unit 300, the data processing device 521 collects and stores information data successively measured with the events.

Figure 8:
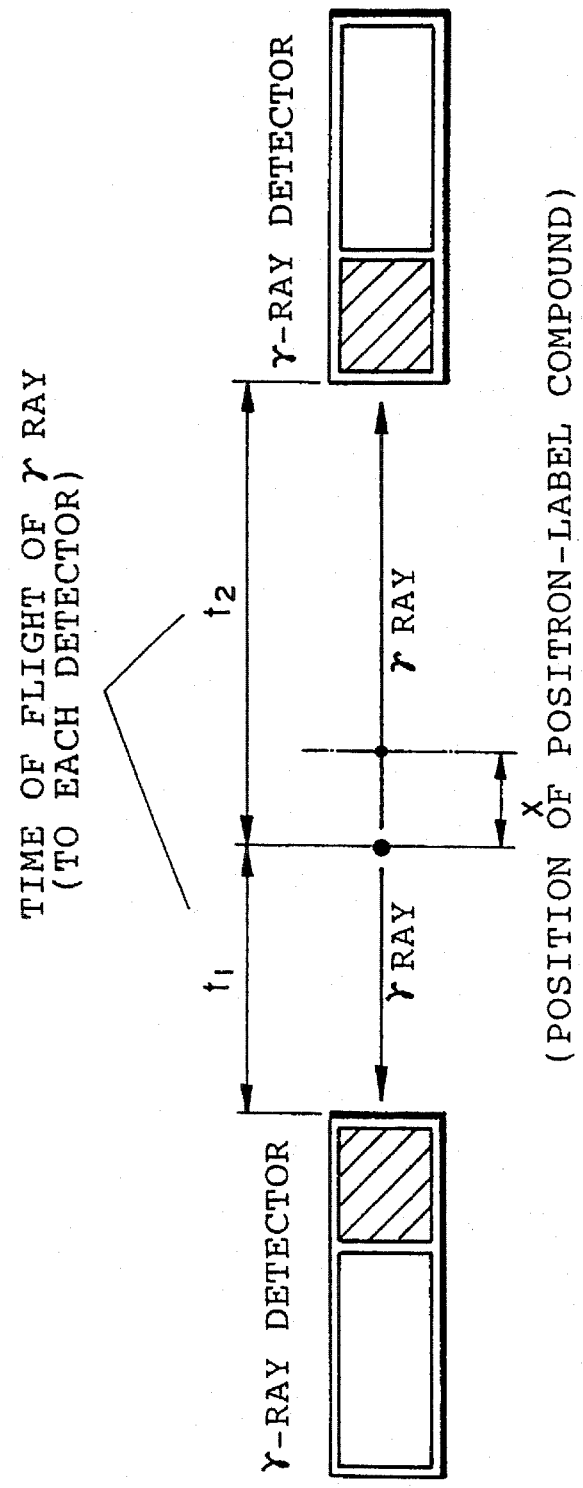
FIG. 8 is an explanatory drawing to illustrate how to calculate an annihilation position by the TOF method.

During or after measurement of annihilation the data processing device 521 processes the thus stored information concerning events by the following procedure to reconstruct an image. First, the device reads out the stored information of one event (which is data with significant bit corresponding to one γ-ray detector in each detector array and time-of-flight difference data), connects the centers of incident surfaces of γ-ray detectors corresponding to the significant bits to calculate a line passing through a position of annihilation occurrence, and thereafter calculates the position of annihilation occurrence on the line based on the time-of-flight difference data (see FIG. 8).

Then the device performs the iterative image restructure operation as expressed by the following formula and processes the data of annihilation occurrence position to obtain a tomographic image by determining approximate convergence.

$$I^{NEW}(x,y) = [I^{OLD}(x,y)/W(x,y)] \times \sum_{K-L} [DATA_{K-L}(t)/[I^{OLD}(x,y)]_{K-L} * R(t)] \quad (1)$$

where x,y: coordinates of pixel;

$I^{NEW}(x,y)$: image after correction by an iterative step;

$I^{OLD}(x,y)$: image before correction of an iterative step;

W(x,y): sampling matrix representing sampling density at pixel (x,y);

K: number of γ-ray detector in one detector array;

L: number of γ-ray detector in the other detector array;

$$\sum_{K-L} [\ ]:$$

sum of values within [ ] for all opposing γ-ray detector pairs;

t: spatial coordinates along a line connecting between a γ-ray detector K and a γ-ray detector L (path K-L);

$DATA_{K-L}(t)$: distribution of annihilation numbers counted on the path K-L;

$[I^{OLD}(x,y)]_{K-L}$: distribution of $I^{OLD}(x,y)$ along the path K-L;

R(t): TOF response function (Gauss function) which is a function of t for a point source response function of temporal resolution of coincidence counting of γ-ray detectors;

*: multiple integration on the path K-L.

Here, the sampling matrix W(x,y) is obtained from the following formula.

$$W(x,y) = \sum_{K-L} 1 \qquad (2)$$

In other words, the number of paths K-L passing through a pixel (x,y) becomes a value at the pixel (x,y).

The above formula (1) effects such a correction that the overall ratio between spatial distribution data of annihilation occurrence measured along the path K-L and spatial distribution data of annihilation occurrence calculated with $I^{OLD}(x,y)$ becomes closer to "1". In this case, W(x,y) functions to correct nonuniformity of sampling density for each pixel and to normalize the corrected value for each pixel. As a result, if the difference between $I^{OLD}(x,y)$ and $I^{NEW}(x,y)$ is small enough, it is judged that correction is made in TOF resolution, presenting an image closer to an actual tomographic image.

Figure 9:
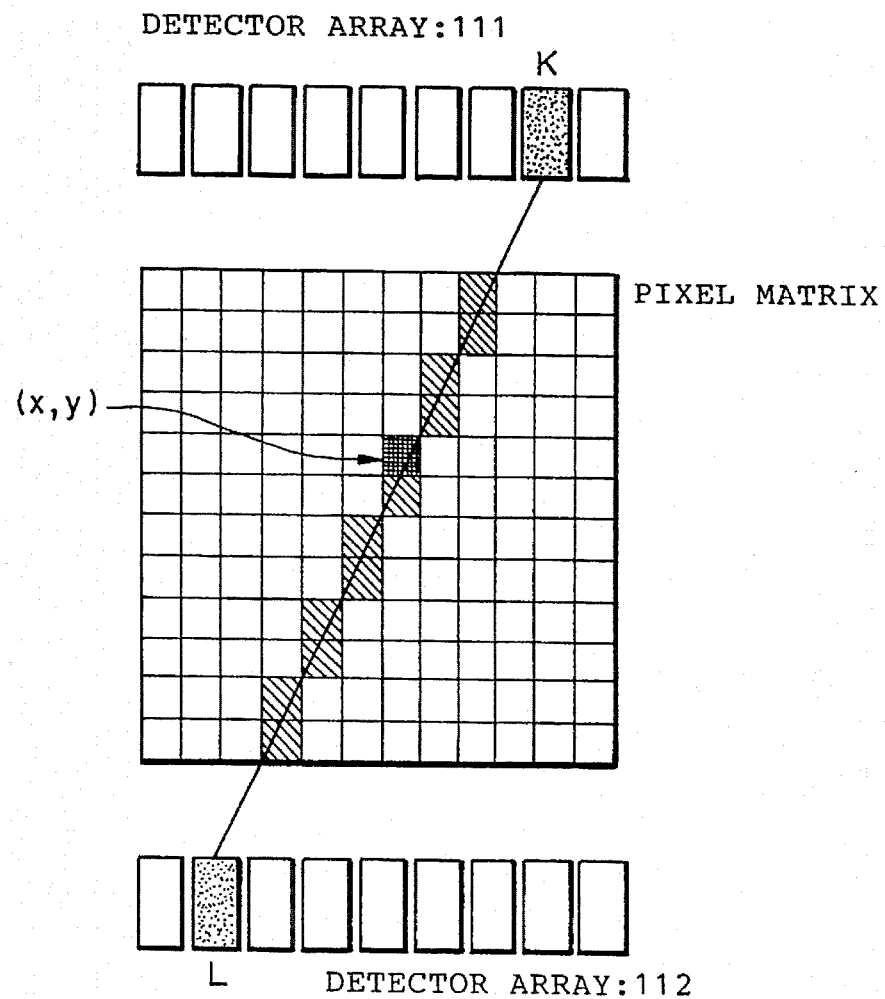
FIGS. 9 and 10 are explanatory drawings to illustrate the iterative reconstructure algorithm.
Figure 10:
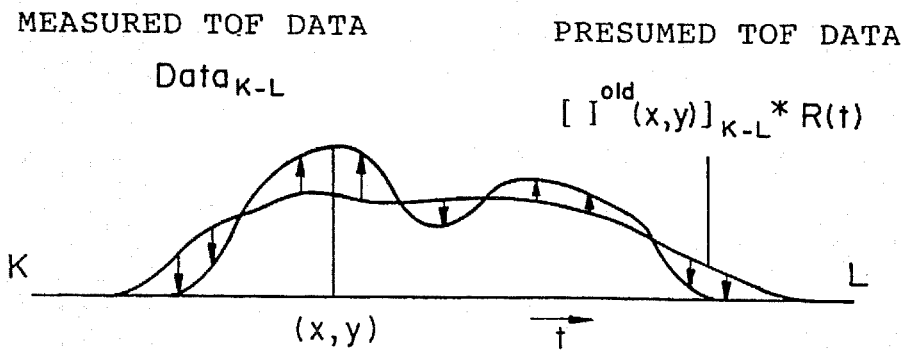

Before starting this iterative process, an initial image is properly set. A typical example, as well as the most popular example, is a method of allocating an average value obtained by dividing the total annihilation number by a pixel number, to all pixels. Next, a first step of iterative process is performed according to the formula (1), using the calculated annihilation occurrence position data. A decision is made as to the coincidence degree based on comparison between $I^{OLD}(x,y)$ and newly obtained $I^{NEW}(x,y)$. A method of this decision is for example the analysis of variance. If the coincidence degree is high, the $I^{OLD}(x,y)$ or $I^{NEW}(x,y)$ is employed as a tomographic image. If the coincidence degree is low, this $I^{NEW}(x,y)$ is set as new $I^{OLD}(x,y)$ and the iterative method is continued in accordance with the formula (1). The above iterative operation and coincidence degree decision are repeated before the coincidence degree becomes sufficiently high or before values of iterative process are converged. The thus obtained values of convergence are employed as a tomographic image (see FIGS. 9 and 10).

The tomographic image is provided to a user by indicating it on the image indicating device 512 or by printing it by the image printing device 513.

Subsequently, moving the detecting unit to scan, the three-dimensional structure of the specific portion can be known. If the detector arrays are arranged in two dimensions, the three-dimensional structure of the specific portion can be observed without scan.

Incidentally, the formula (1) is effective to cases where the statistical noise and errors of measured data are small, but is likely to emphasize noise and errors if the measured data includes large noise or errors. Accordingly, if the noise or errors are large or if the amplitude of noise or errors is unknown, it is practical to perform the iterative process using the following formula.

$$I^{NEW}(x,y) = [I^{OLD}(x,y)/W(x,y)] \times \qquad (3)$$
$$[\Sigma[[DATA_{K-L}(t)/[I^{OLD}(x,y)]_{K-L}*R_1(t)]]*R_2(t)]$$

where $R_1(t)$: Gauss function with smaller half width than R(t);

$R_2(t)$: correction function.

$R_1(t)$ in the formula (3) is smaller in half width than R(t) in the formula (1), so that the correction effect of TOF resolution is decreased and the resolution of image is lowered, but the statistical noise is reduced. Also, $R_2(t)$ functions to smooth correction values along each path and thereby to suppress high-frequency components of statistical noise accompanying the correction values, having a relatively large width, and is generally a Gauss function. The greater the width of $R_2(t)$, the higher the noise suppressing effect, but the speed of convergence becomes slower. $R_1(t)$ and $R_2(t)$ are determined taking into consideration the measurement system, the measurement time and the measured object.

The TOF resolution is normally lower than the spatial resolution determined by the size of receiving surface of γ-ray detectors. However, the execution of the above iterative process effects statistical correction considering the TOF resolution, so that the result is the same as that with improved TOF resolution.

The present embodiment can be modified in the structure of the detecting unit like the second and third embodiments for the first embodiment, attaining the same effects.

It should be noted that the present invention is by no means limited to the above embodiments but can be modified in variety. For example, the specific portion as a measured object is not limited to the brain or the heart, but may be for example a liver or a kidney. Also, the material for scintillators is not limited to $BaF_2$ but may be CsF. Further, the two detector arrays constituting the detecting unit may be so arranged as to become optimum according to the specific portion of measured object.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. A positron imaging apparatus comprising:

a first detector array comprising a first number of γ-ray detectors with a first detector size;

a second detector array arranged as opposed to said first detector array interposing an object to be measured therebetween, comprising a second number of γ-ray detectors with a second detector size;

annihilation presuming means for receiving a signal reflecting energy of incident γ-ray, output from said first detector array and a signal reflecting energy of incident γ-ray, output from said second detector array, to obtain a presumable γ-ray pair emitted with positron annihilation; and image reconstructing means for, in synchronization with annihilation occurrence notification output from said annihilation presuming means, collecting and storing receiving detector information on said first detector array and receiving detector information on said second detector array for the presumed γ-ray pair emitted with positron annihilation and performing an arithmetic operation according to a predetermined image reconstruction algorithm based on information of a line passing through a position of annihilation occurrence calculated from the stored detector information;

wherein in operation, a specific portion of the object is located close to said first detector array, the first number is smaller than the second number and coincidence counting is carried out for every opposing γ-ray detector pair.

2. A positron imaging apparatus according to claim 1, wherein said predetermined image reconstruction algorithm is the focal plane method, in which a virtual focal plane is first set, thereafter an intersection is obtained between said virtual focal plane and a line passing through said position of each annihilation occurrence, and an image is reconstructed considering the degree of concentration in a distribution of said intersections.

3. A positron imaging apparatus according to claim 1, further comprising a driving means for moving said first detector array and said second detector array to scan the measured object.

4. A positron imaging apparatus comprising:

a first detector array comprising a first number of γ-ray detectors with a first detector size;

a second detector array arranged as opposed to said first detector array interposing an object to be measured therebetween, said second detector array comprising a second number of γ-ray detectors with a second detector size;

annihilation presuming means for receiving signals reflecting energy and timing of incident γ-rays, output from said first detector array and said second detector array, to obtain a presumable γ-ray pair emitted with positron annihilation;

time-of-flight difference measuring means for measuring a time between a γ-ray arrival time at said first detector array and a γ-ray arrival time at said second detector array with regard to detection signals of two γ-rays with annihilation, output from said first detector array and said second detector array; and image reconstructing means for, in synchronization with annihilation occurrence notification output from said annihilation presuming means, collecting receiving detector information on said first detector array and receiving detector information on said second detector array for the presumable γ-ray pair emitted with positron annihilation, and time-of-flight difference information output from said time-of-flight difference measuring means, calculating a position of annihilation occurrence using said receiving detector information and said time-of-flight difference information, storing said annihilation occurrence position, and performing an arithmetic operation according to a predetermined image reconstruction algorithm based on acquired data;

wherein in operation, a specific portion of the object is located close to said first detector array, the first number is smaller than the second number and coincidence counting is carried out for every opposing γ-ray detector pair.

5. A positron imaging apparatus according to claim 4, wherein said predetermined image reconstruction algorithm is the iterative process, in which correction of image is iteratively conducted taking into consideration the spatial resolution at said stored annihilation occurrence position.

6. A positron imaging apparatus according to claim 4, further comprising a driving means for moving said first detector array and said second detector array to scan the measured object.

7. A positron imaging apparatus comprising:

a first detector array comprising a first number of γ-ray detectors with a first detector size;

a second detector array arranged as opposed to said first detector array interposing an object to be measured therebetween, comprising a second number of γ-ray detectors with a second detector size;

annihilation presuming means for receiving a signal reflecting energy of incident γ-ray, output from said first detector array and a signal reflecting energy of incident γ-ray, output from said second detector array, to obtain a presumable γ-ray pair emitted with positron annihilation; and image reconstructing means for, in synchronization with annihilation occurrence notification output from said annihilation presuming means, collecting and storing receiving detector information on said first detector array and receiving detector information on said second detector array for the presumed γ-ray pair emitted with positron annihilation and performing an arithmetic operation according to a predetermined image reconstruction algorithm based on information of a line passing through a position of annihilation occurrence calculated from the stored detector information;

wherein in operation, a specific portion of the object is located close to said first detector array, the first detector size is smaller than the second detector size and coincidence counting is carried out for every opposing γ-ray detector pair.

8. A positron imaging apparatus according to claim 7, wherein said predetermined image reconstruction algorithm is the focal plane method, in which a virtual focal plane is first set, thereafter an intersection is obtained between said virtual focal plane and a line passing through said position of each annihilation occurrence, and an image is reconstructed considering the degree of concentration in a distribution of said intersections.

9. A positron imaging apparatus according to claim 7, further comprising a driving means for moving said first detector array and said second detector array to scan the measured object.

10. A positron imaging apparatus comprising:

a first detector array comprising a first number of γ-ray detectors with a first detector size;

a second detector array arranged as opposed to said first detector array interposing an object to be measured therebetween, comprising a second number of γ-ray detectors with a second detector size;

annihilation presuming means for receiving signals reflecting energy and timing of incident γ-rays, output from said first detector array and said second detector array, to obtain a presumable γ-ray pair emitted with positron annihilation;

time-of-flight difference measuring means for measuring a time between a γ-ray arrival time at said first detector array and a γ-ray arrival time at said second detector array with regard to detection signals of two γ-rays with annihilation, output from said first detector array and said second detector array; and image reconstructing means for, in synchronization with annihilation occurrence notification output from said annihilation presuming means, collecting receiving detector information on said first detector array and receiving detector information on said second detector array for the presumable γ-ray pair emitted with positron annihilation, and time-of-flight difference information output from said time-of-flight difference measuring means, calculating a position of annihilation occurrence using said receiving detector information and said time-of-flight difference information, storing said annihilation occurrence position, and performing an arithmetic operation according to a predetermined image reconstruction algorithm based on acquired data;

wherein in operation, a specific portion of the object is located close to said first detector array, the first detector size is smaller than the second detector size and coincidence counting is carried out for every opposing γ-ray detector pair.

11. A positron imaging apparatus according to claim 10, wherein said predetermined image reconstruction algorithm is the iterative process, in which correction of image is iteratively conducted taking into consideration the spatial resolution at said stored annihilation occurrence position.

12. A positron imaging apparatus according to claim 10, further comprising a driving means for moving said first detector array and said second detector array to scan the measured object.

13. A positron imaging apparatus comprising:

a first detector array comprising a first number of γ-ray detectors with a first detector size;

a second detector array arranged as opposed to said first detector array interposing an object to be measured therebetween, comprising a second number of γ-ray detectors with a second detector size;

annihilation presuming means for receiving a signal reflecting energy of incident γ-ray, output from said first detector array and a signal reflecting energy of incident γ-ray, output from said second detector array, to obtain a presumable γ-ray pair emitted with positron annihilation; and image reconstructing means for, in synchronization with annihilation occurrence notification output from said annihilation presuming means, collecting and storing receiving detector information on said first detector array and receiving detector information on said second detector array for the presumed γ-ray pair emitted with positron annihilation and performing an arithmetic operation according to a predetermined image reconstruction algorithm based on information of a line passing through a position of annihilation occurrence calculated from the stored detector information;

wherein in operation, a specific portion of the object is located close to said first detector array, the detector pitch of the γ-ray detectors in said first detector array is smaller than the detector pitch of the γ-ray detectors in said second detector array and coincidence counting is carried out for every opposing γ-ray detector pair.

14. A positron imaging apparatus according to claim 13, wherein said predetermined image reconstruction algorithm is the focal plane method, in which a virtual focal plane is first set, thereafter an intersection is obtained between said virtual focal plane and a line passing through said position of each annihilation occurrence, and an image is reconstructed considering the degree of concentration in a distribution of said intersections.

15. A positron imaging apparatus according to claim 13, further comprising a driving means for moving said first detector array and said second detector array to scan the measured object.

16. A positron imaging apparatus comprising:

a first detector array comprising a first number of γ-ray detectors with a first detector size;

a second detector array arranged as opposed to said first detector array interposing an object to be measured therebetween, comprising a second number of γ-ray detectors with a second detector size;

annihilation presuming means for receiving signals reflecting energy and timing of incident γ-rays, output from said first detector array and said second detector array, to obtain a presumable γ-ray pair emitted with positron annihilation;

time-of-flight difference measuring means for measuring a time between a γ-ray arrival time at said first detector array and a γ-ray arrival time at said second detector array with regard to detection signals of two γ-rays with annihilation, output from said first detector array and said second detector array, and image reconstructing means for, in synchronization with annihilation occurrence notification output from said annihilation presuming means, collecting receiving detector information on said first detector array and receiving detector information on said second detector array for the presumable γ-ray pair emitted with positron annihilation, and time-of-flight difference information output from said time-of-flight difference measuring means, calculating a position of annihilation occurrence using said receiving detector information and said time-of-flight difference information, storing said annihilation occurrence position, and performing an arithmetic operation according to a predetermined image reconstruction algorithm based on acquired data;

wherein in operation, a specific portion of the object is located close to said first detector array, the detector pitch of the γ-ray detectors in said first detector array is smaller than the detector pitch of the γ-ray detectors in said second detector array and coincidence counting is carried out for every opposing γ-ray detector pair.

17. A positron imaging apparatus according to claim 16, wherein said predetermined image reconstruction algorithm is the iterative process, in which correction of image is iteratively conducted taking into consideration the spatial resolution at said stored annihilation occurrence position.

18. A positron imaging apparatus according to claim 16, further comprising a driving means for moving said first detector array and said second detector array to scan the measured object.

* * * * *